US009200961B2

(12) United States Patent
Angel et al.

(10) Patent No.: US 9,200,961 B2
(45) Date of Patent: Dec. 1, 2015

(54) SYSTEMS AND METHODS FOR HIGH RESOLUTION SPATIAL HETERODYNE RAMAN SPECTROSCOPY (71) Applicant: University of South Carolina, Columbia, SC (US)

(72) Inventors: Stanley Michael Angel, Columbia, SC (US); Jerry Chance Carter, Livermore, CA (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 14/067,244

(22) Filed: Oct. 30, 2013

(65) Prior Publication Data
US 2014/0247447 A1 Sep. 4, 2014

Related U.S. Application Data (60) Provisional application No. 61/720,165, filed on Oct. 30, 2012.

(51) Int. Cl.
*G01J 3/45* (2006.01)
*G01J 3/44* (2006.01)
*G01J 3/14* (2006.01)
*G01J 3/453* (2006.01)
*G01N 21/65* (2006.01)

(52) U.S. Cl.
CPC .... *G01J 3/44* (2013.01); *G01J 3/14* (2013.01); *G01J 3/4531* (2013.01); *G01N 21/65* (2013.01); *G01J 2003/451* (2013.01)

(58) Field of Classification Search
CPC ............. G01J 3/0256; G01J 3/44; G01J 3/45; G01J 2003/451; G01J 3/4531; G01J 3/4532; G01J 2003/4538; G01J 3/14; G01N 21/65; G01N 2021/655
USPC ......................................... 356/484, 451, 456
See application file for complete search history.

(56) References Cited

U.S. PATENT DOCUMENTS

| | | | | |
|---|---|---|---|---|
| 5,059,027 A * | 10/1991 | Roesler et al. | ................ | 356/456 |
| 8,154,732 B2 * | 4/2012 | Bodkin et al. | ................ | 356/484 |
| 2007/0159634 A1 * | 7/2007 | Englert | ........................ | 356/450 |
| 2009/0231592 A1 * | 9/2009 | Harlander et al. | ............ | 356/456 |
| 2011/0222048 A1 * | 9/2011 | Englert et al. | ................ | 356/28.5 |
| 2013/0188181 A1 * | 7/2013 | Angel et al. | ................... | 356/301 |

OTHER PUBLICATIONS

Gomer et al., Raman Spectroscopy Using a Spatial Heterodyne Spectrometer: Proof of Concept, 2011, Soceity of Applied Spectroscopy, vol. 65, No. 8, pp. 849-857.*
Nathaniel et al., "Spatial Heterodyne Raman Spectroscopy", $42_{nd}$ Lunar and Planetary Science Conference, Mar. 7-11, 2011, The Woodlands, Texas—2 pages.

* cited by examiner

*Primary Examiner* — Tarifur Chowdhury
*Assistant Examiner* — Michael P Lapage
(74) *Attorney, Agent, or Firm* — Dority & Manning, P.A.

(57) ABSTRACT

The present subject matter is directed to a device for spectroscopy. The device includes an excitation source and a first spatial heterodyne spectrometer configured to receive wavelengths from the excitation source and filter the wavelengths to produce fringes on a sample. The device also includes a second heterodyne spectrometer configured to receive Raman wavelengths from the sample.

21 Claims, 9 Drawing Sheets

SYSTEMS AND METHODS FOR HIGH RESOLUTION SPATIAL HETERODYNE RAMAN SPECTROSCOPY

CROSS-REFERENCE TO RELATED APPLICATION

The present application is based on and claims priority to U.S. Provisional Application 61/720,165 having a filing date of Oct. 30, 2012, which is incorporated by reference herein.

GOVERNMENT SUPPORT CLAUSE

This invention was made with government support under CHE-0526821 awarded by the National Science Foundation. Therefore, the government has certain rights in the invention.

BACKGROUND

Figure 1:
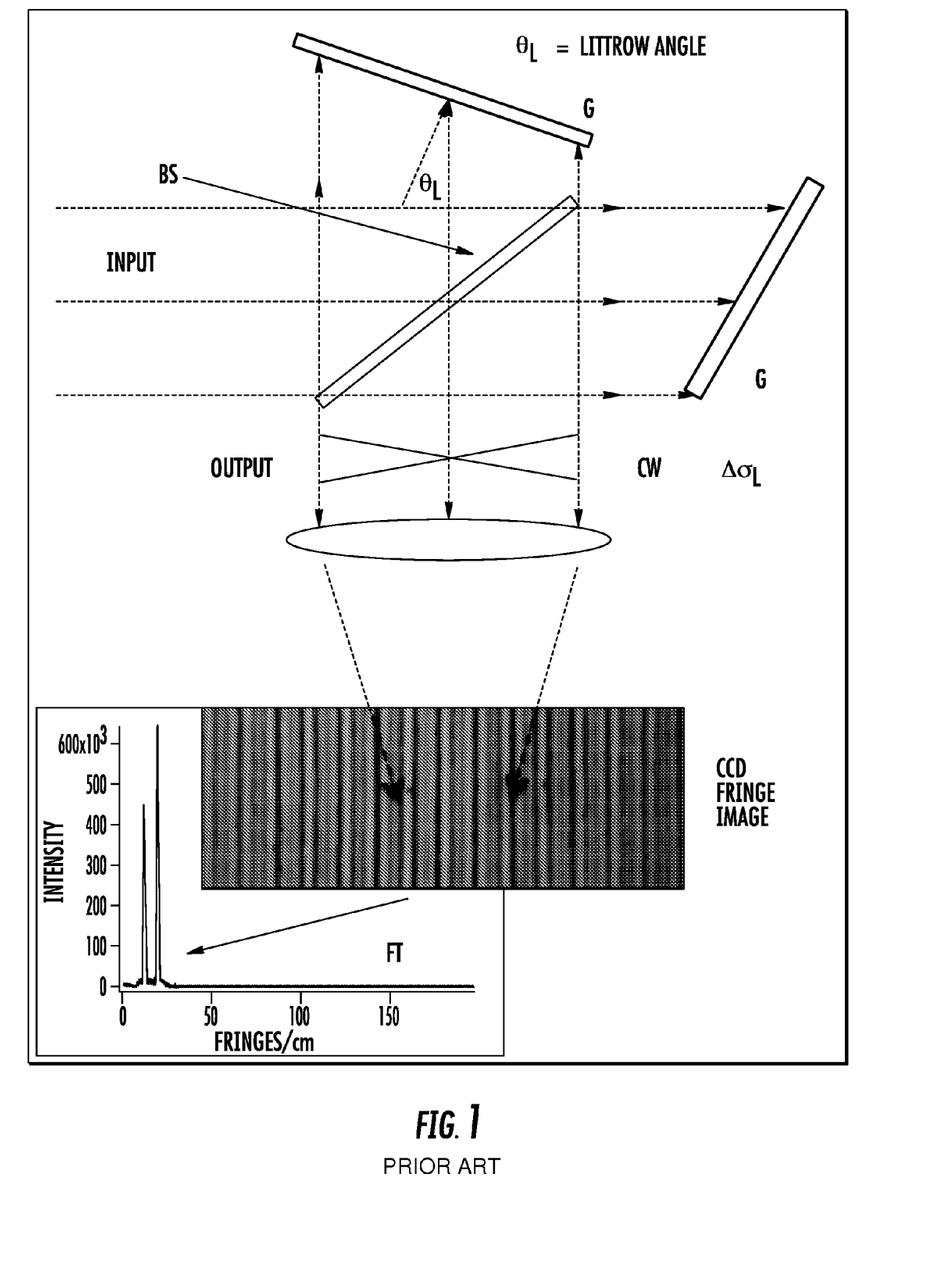
FIG. 1, depicts a basic SHS design in accordance with certain aspects of the present disclosure.

The spatial heterodyne spectrometer (SHS) design (FIG. 1 is an exemplary illustration) is compatible with pulsed laser excitation and offers several advantages including high spectral resolution, limited by the diffraction gratings, in a very small form factor; very high optical etendue and thus high throughput; and demonstrated high resolution in the UV. Applications of spatial heterodyne spectrometers (SHS) outside of astronomy are still relatively few; however a UV absorption SHS spectrometer has been successfully demonstrated in space on STS 112.6 The basic SHS design is like a Michelson interferometer but with tilted diffraction gratings and no moving parts and like a Michelson there is no input slit. The SHS offers a wide acceptance angle at the grating (e.g., 1° or 10° using field widening prisms) and thus a wide-area measurement capability, high light throughput and imaging capabilities.

The spatial heterodyne spectrometer was only recently described for Raman applications, likely because SHS technology has been focused on astronomical remote sensing and because most systems are designed for a very small spectral band pass. However, the SHS spectrometer design is ideal for Raman, especially deep-UV Raman spectroscopy. The use of diffraction gratings in the SHS interferometer design provides much higher resolution in the UV, even with the relatively few samples provided by the charge-coupled device (CCD) detector, and good control over the spectral range.

Figure 2:
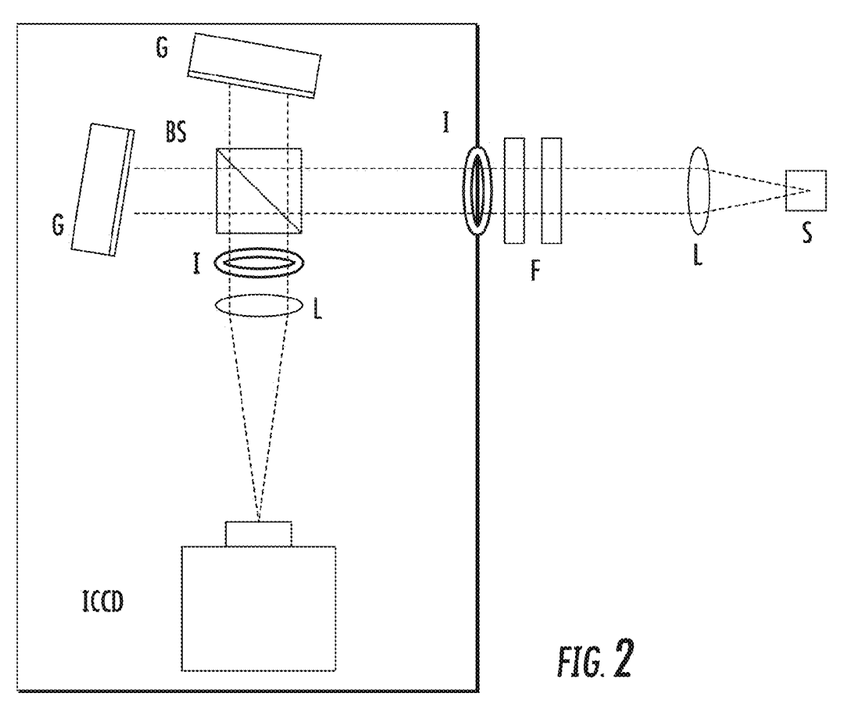
FIG. 2 depicts a schematic of SHS Raman spectrometer system layout in accordance with certain aspects of the present disclosure ((L) Lens, (G) grating, (BS) beam splitter, (F) laser rejection filter, (I) iris/aperture, (S) sample holder, and (ICCD) intensified charge-coupled device or (CCD) charge coupled device, the laser is not shown here but the beam is focused onto the sample from the top)

As described by the inventors in U.S. application Ser. No. 13/654,924, incorporated by reference herein, the Raman scattered light is collected and collimated, then filtered by the two holographic filters to remove laser scatter from the Raman signal (an exemplary embodiment is shown in FIG. 2). The filtered, collimated light passes through a 25-mm aperture into the SHS. Light entering the SHS is split into two beams by the 50/50 beam splitter. The separated beams strike the tilted diffraction gratings, are diffracted back along the same direction, re-enter the beam splitter, and recombine. The grating tilt angle defines the Littrow wavenumber, $\sigma_L$, the wavenumber at which both beams exactly retro-reflect, producing no constructive or destructive interference and therefore no fringe pattern at the detector. For any wavelength other than Littrow, the recombined light produces a crossed wave front, of which the crossing angle is wavenumber dependent, and produces an interference pattern at the interferometer output, which is the Fourier transform of the Raman spectrum. The interference pattern imaged onto the ICCD or CCD detector produces an image of vertical fringes. The number of fringes, f, across the ICCD is related to the Littrow wavenumber by Eqn. 1:

$$f = 4*(\sigma - \sigma_L)*\tan\theta_L, \qquad \text{Eqn. 1}$$

where f is in fringes/cm, $\sigma$ is the wavenumber of interest, $\sigma_L$ is the Littrow wavenumber and $\theta_L$ is the Littrow angle. Bands with larger wavenumber shifts produce more closely spaced fringes. Because of the symmetry in this equation, spectral features at wavenumbers both higher and lower than Littrow overlap on the detector. In the case of Raman spectra, this can cause overlap of Stokes and anti-Stokes bands if the Littrow wavelength is set near the laser excitation wavelength. However, this overlap can be avoided by tilting one grating, producing a rotation of the fringe pattern clockwise for bands at wavenumbers below the Littrow wavelength and counter-clockwise for bands above Littrow. A 2D Fourier transform (FT) of the resulting interferogram recovers both spectra, above and below the Littrow wavelength. The use of a 2D FT to recover independent spectral information in the vertical and horizontal dimensions of the interferogram can be used to double the spectral range of the SHRS without additional samples and it can also be used for 2D imaging as described below.

A small UV Raman spectrometer is a particular technical challenge using dispersive (grating) approaches and requires large spectrographs and very narrow slits to achieve the spectral resolution required for many applications. The heterodyne approach of the SHS has only a weak coupling of resolution and throughput, so a high resolution UV SHRS can both be small, and employ a wide aperture to maximize throughput. The SHRS measures all optical path differences in its interferogram simultaneously with a detector array, so the technique is compatible with gated detection using pulsed lasers, important to reject ambient background and mitigate fluorescence (already low in the UV) that is encountered for most "real" samples. In the SHRS, the spectrum is heterodyned around the laser wavelength, making it particularly suitable for Raman measurements.

As such, it would be desirable to provide suitable systems and methods for small sized Raman spectroscopy to measure biomarkers and other samples of interest such as minerals, water, $CO_2$ ice, or the like.

SUMMARY

Aspects and advantages of the invention will be set forth in part in the following description, or may be obvious from the description, or may be learned through practice of the invention.

In one aspect, the present subject matter is directed to a device for spectroscopy. The device includes an excitation source and a first spatial heterodyne interferometer configured to receive wavelengths from the excitation source and filter the wavelengths to produce fringes on a sample. The device also includes a second heterodyne interferometer configured to receive Raman wavelengths from the sample.

In yet another aspect of the present disclosure, a method of spectroscopy is described.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

The present disclosure is generally directed to systems and methods for spatial heterodyne Raman spectroscopy. More specifically, the present disclosure describes miniature deep-UV Raman spectrometers of small size, with high spectral resolution, a large spectral range and with high light throughput. The miniature, high performance, UV Raman spectrometers described herein permit consideration of integrating one or several Raman spectrometers into a chemical process stream, on an integrated optical device, or consideration of sending robust Raman spectrometers to remotely located samples using robotic vehicles such as a planetary lander or unmanned underwater vehicle. The disclosed system has no moving parts and is compatible with pulsed laser excitation and gated detection, allowing monitoring of fast chemical and electronic processes. The spectrometer design inherently allows imaging, including 1D line imaging and true 2D imaging.

The small size and UV spectroscopic performance of the described devices substantially broaden the applicability of Raman for on-line, in-situ, in-vivo, and standoff measurements, in wide-ranging applications such as chemical process monitoring, on-line chemical diffusion measurements, confocal microRaman imaging of biological tissues and cells, standoff forensics analysis, planetary exploration, hand held geological measurements, deep-ocean oceanographic measurements, electronics device characterization, and many others which would benefit from the use of a miniature high-resolution UV Raman spectrometer with imaging and a wide-area measurement capability.

The present disclosure describes a spatial heterodyne interferometer having a design with no moving parts. Spatial heterodyne spectrometers (SHS) have previously been described with designs that are compatible with pulsed laser excitation and offering several advantages including high spectral resolution, limited by the diffraction gratings, in a very small form factor; a large acceptance angle; very high optical etendue and thus high throughput; and demonstrated high resolution in the UV. Applications of spatial heterodyne spectrometers (SHS) outside of astronomy are still relatively few; however, a UV absorption SHS spectrometer has been successfully demonstrated in space. As described in the present disclosure, the ability to heterodyne using diffraction gratings (or prisms) in the SHS design provides much higher resolution in the UV and better control over the spectral range. Advantages of the proposed SHS UV Raman system, other than the small size, is no moving parts, making it compatible with a pulsed laser and gated detector, essential for daylight measurements, wide-area detection and wide acceptance angle, large spectral range, high resolving power and thus high spectral resolution, and high optical throughput.

In accordance with the present disclosure, a SHS Raman spectrometer (also referred to herein as SHRS) can be utilized for Raman measurements on liquid, solid, and gas samples using visible (532 nm), near-infrared, UV, or deep-UV laser excitation.

In previously discussed U.S. application Ser. No. 13/654,924, incorporated by reference herein, a SHRS spectrometer is disclosed using 532 nm excitation and 25.4-mm wide, 150 gr/mm groove density diffraction gratings. The measured resolution of diamond with this system, 5 cm$^{-1}$ using 244-nm excitation, was very close to the theoretically predicted resolution, 4.7 cm$^{-1}$, as shown in FIG. 3.

Figure 3:
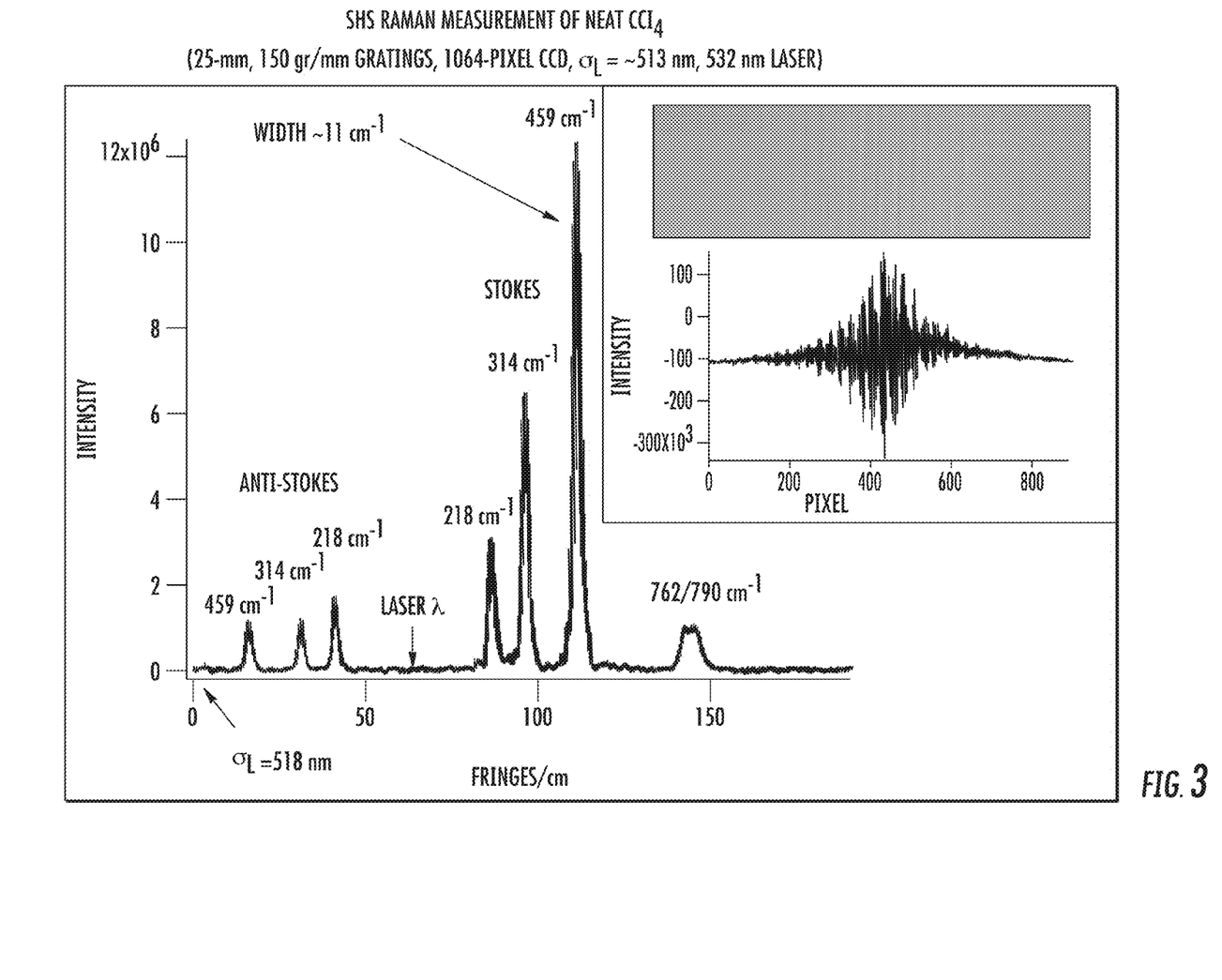
FIG. 3 depicts a fringe image, the image cross-section, and a Raman spectrum (plotted as Raman scattering intensity versus fringes/cm, f) in accordance with certain aspects of the present disclosure.

FIG. 3 illustrates a fringe image, the image cross-section, and a Raman spectrum (plotted as Raman scattering intensity versus fringes/cm, f) that was generated by taking a one-dimensional (1D) Fourier transform of the fringe cross-section for carbon tetrachloride (CCl$_4$). The CCl$_4$ spectrum shown in FIG. 3 includes both Stokes and anti-Stokes Raman bands though they almost completely overlap because of the Littrow wavelength setting.

Figure 4:
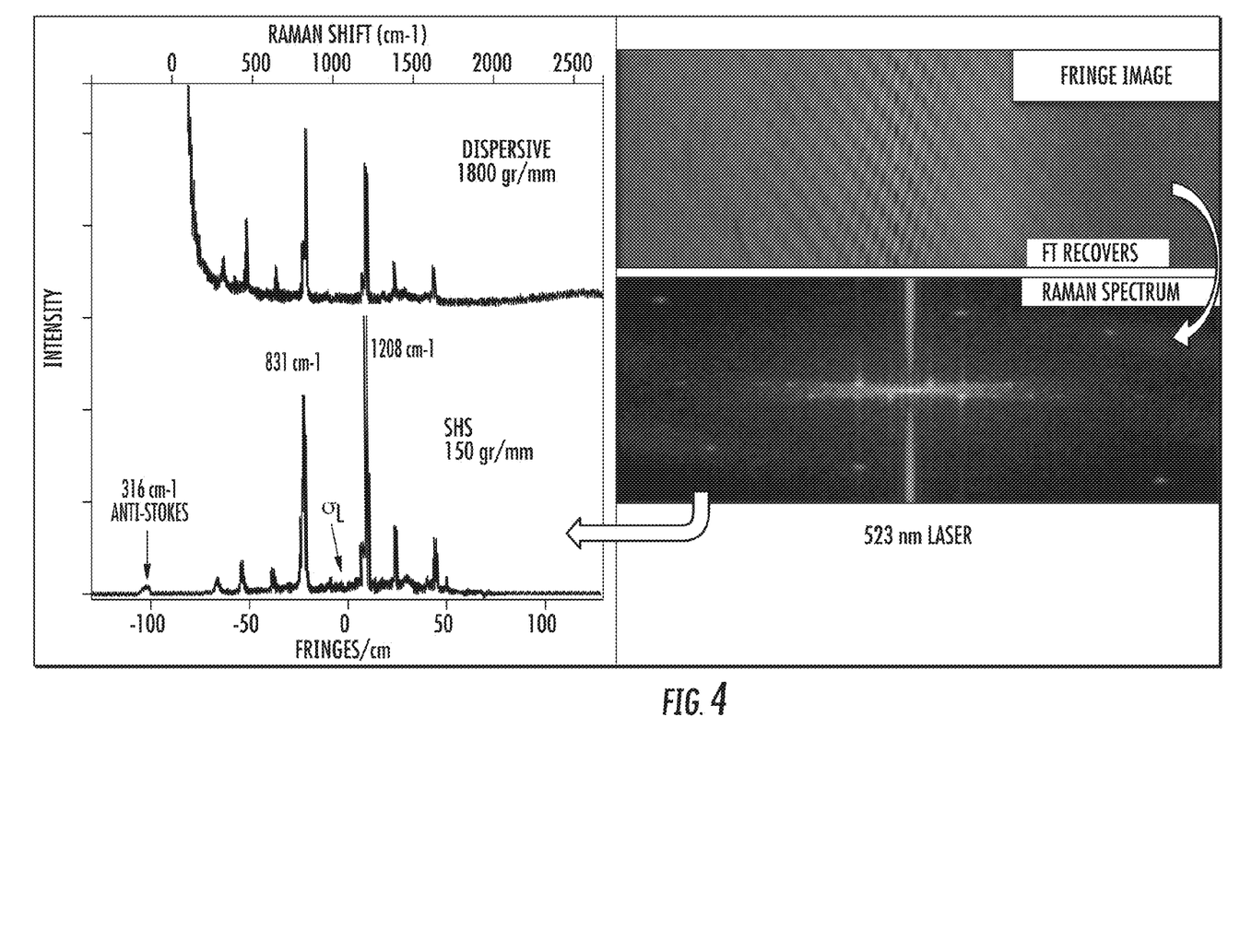
FIG. 4 depicts the SHS Raman spectrum of p-xylene using the tilted grating technique in accordance with certain aspects of the present disclosure.

FIG. 4 illustrates the SHS Raman spectrum of p-xylene using the tilted grating technique to double the useful range. For this measurement the Littrow wavelength was set between the two strongest bands at 831 cm$^{-1}$ and 1208 cm$^{-1}$. Bands below Littrow (negative f, fringes/cm) produced fringes that were rotated clockwise and bands above Littrow rotated the fringes counter-clockwise. A 2D FFT analysis was used to separate the two spectral regions as shown in the spectrum. For comparison a Raman spectrum of p-xylene using the dispersive system is also shown.

Figure 5:
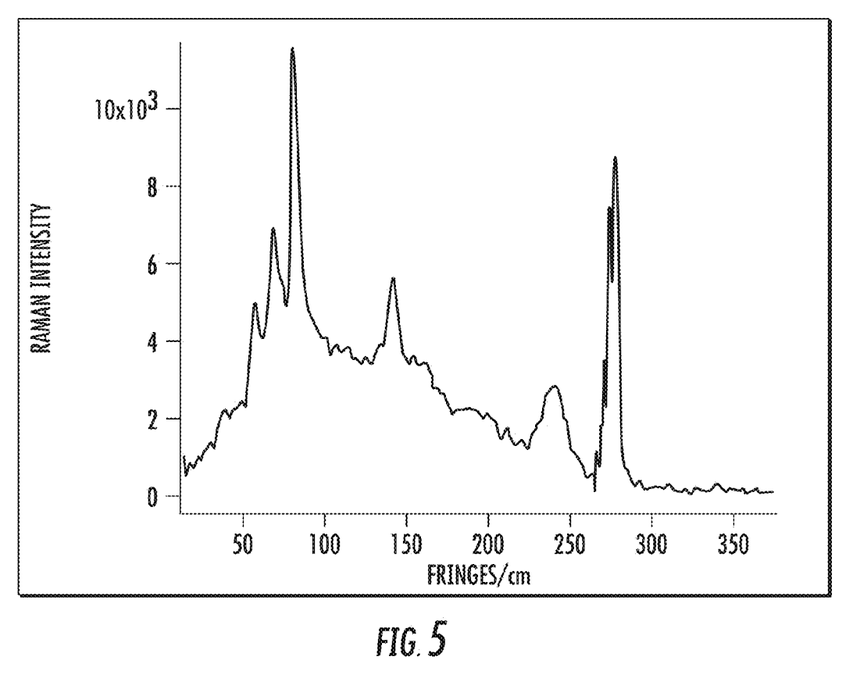
FIG. 5 depicts the use of the SHRS to measure the resonance Raman spectrum of 6-ppm β-carotene using 25.4-mm 150 gr/mm gratings and 532 nm excitation in accordance with certain aspects of the present disclosure.

FIG. 5 illustrates the use of the SHRS to measure the resonance Raman spectrum of 6-ppm b-carotene using 25.4-mm 150 gr/mm gratings and 532 nm excitation.

Figure 6:
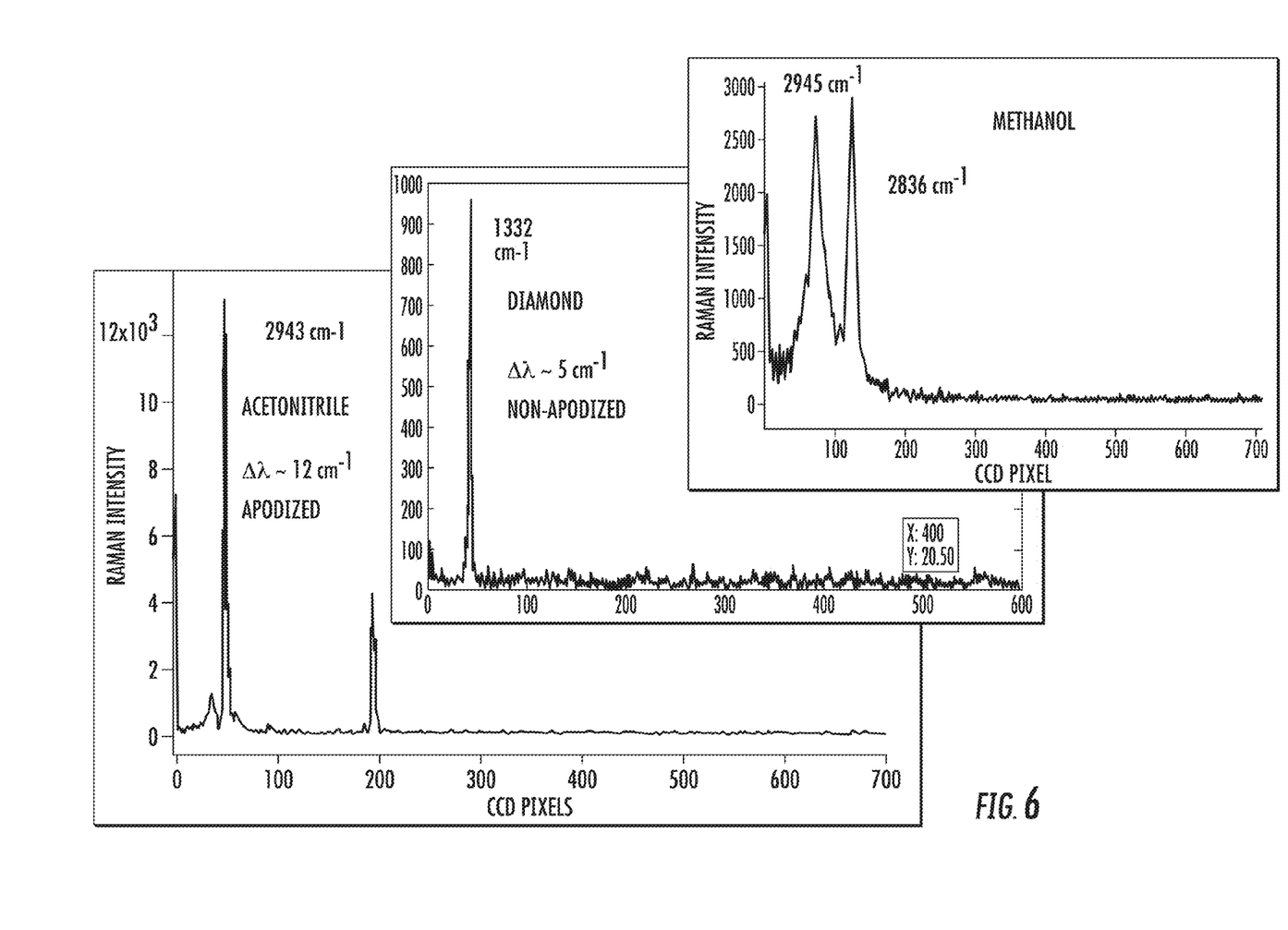
FIG. 6 depicts Raman spectra of acetonitrile, diamond and methanol using 25.4 mm, 300 gr/mm gratings and 244-nm excitation in accordance with certain aspects of the present disclosure.

An SHRS was used to measure deep-UV Raman spectra of a variety of samples using ~5 mW of 244-nm excitation. FIG. 6 illustrates Raman spectra of acetonitrile, diamond and methanol using 25.4 mm, 300 gr/mm gratings and 244-nm excitation. The width of the diamond Raman band was measured to be 5 cm$^{-1}$, very close to the theoretical resolution of 4.7 cm$^{-1}$.

The present disclosure describes a SHRS system that is half the size of previously described systems. The spectral resolution of the SHRS does not depend on a slit and is not a strong function of spectrometer size. At a given wavenumber the resolving power, R, is determined by the total number of grooves illuminated on the two gratings. This is equivalent to a dispersive monochromator using infinitely narrow slits, but with much higher light throughput in the case of the SHRS, because there is no slit. The heterodyning nature of the SHRS provides extremely high spectral resolution, much higher than a typical Raman spectrum demands, and in previous work, relatively small, 25.4-mm, course-ruled 150-gr/mm diffraction gratings were utilized to reduce the resolution enough to obtain a large Raman spectral range. An alternative approach described herein is to use much smaller gratings with higher groove densities, in order to optimize both the spectral resolution and range while simultaneously reducing the size of the spectrometer.

The fundamental limit for the minimum size of a diffraction grating in the SHRS is determined by the size or angular extent of the Airy disc produced by diffraction of light. The Rayleigh criterion, $\sin(\theta_{min})=1.22\lambda/D$, can be used to estimate the minimum diffraction angle, $\theta_{min}$, that can be resolved by an optical element of size D, where $\lambda$ is the wavelength of the Raman scattered beam. The angle that needs to be resolved depends on the desired spectral resolution (e.g., 5 cm$^{-1}$) and change in diffraction angle that corresponds to the desired resolution element. The diffraction angle change per resolution element depends on the grating groove density. The maximum groove density for diffraction corresponds to a groove spacing that is no smaller than half the wavelength. Thus, the theoretical maximum groove density for 785 nm, 532 nm and 244 nm excitation, is approximately 2350 gr/mm, 3760 gr/mm, and 8000 gr/mm, respectively. These groove densities are not necessarily practical however, as the diffraction angle must be below 90°, but these numbers provide guidance to the limiting groove density for a miniature spectrometer.

To achieve 5 cm$^{-1}$ spectral resolution for a 1000 cm$^{-1}$ Raman shift using 244 nm excitation requires an angular resolving power of 0.0057° using a 2400 gr/mm diffraction grating. The Rayleigh criterion places a lower limit on the size of the diffraction grating of about 3 mm to achieve Raman spectra with 5 cm$^{-1}$ resolution using a 244-nm laser. Below this minimum size the spectral resolution will suffer. However, a smaller grating size can be used by increasing the grating groove density. Also, it should be pointed out that 244-nm is worst case in terms of the minimum grating size. Much smaller gratings can be used to achieve 5 cm$^{-1}$ resolution if longer wavelength lasers (e.g., 532 nm or 785 nm) are used for excitation.

Table 1 shows the minimum grating size, $D_{min}$, based on the Rayleigh criterion that can be used to achieve 5 cm$^{-1}$ resolution for 244 nm and 532 nm excitation for a variety of diffraction grating groove densities. The groove densities shown are near the upper limit that should be considered for these wavelengths. It is interesting to consider that at the theoretical limit of groove density, the minimum size grating that is theoretically possible, should approach the diffraction limited slit width in a monochromator of similar resolution, while at the same time the SHRS throughput (e.g., etendue) decreases to a value similar to that of the same monochromator, but at a tiny fraction of the size.

The results in Table 1 show that the Airy disc is not limiting in the development of mm size deep UV SHRS spectrometers with 5 cm$^{-1}$ spectral resolution.

TABLE 1

Minimum grating size, Dmin, for 5 cm$^{-1}$ resolution at the indicated laser excitation wavelengths, for different diffraction grating grove densities.

| Gr/mm | Littrow 1 (244 nm) | Dq (244 nm)* | $D_{min}$ | Littrow 1 (532 nm) | Dq (532 nm)* | $D_{min}$ |
|---|---|---|---|---|---|---|
| 2400 | 17.45° | 0.0057° | 3.1 mm | 42.36° | 0.0293° | 1.3 mm |
| 3600 | 26.75° | 0.0072° | 2.4 mm | — | — | |
| 4800 | 36.89° | 0.011° | 1.6 mm | — | — | |

*angular resolving power for 5 cm$^{-1}$ spectral resolution.

Several SHRS spectrometers, using ½-inch (12.5 mm), ¼-inch (6.75 mm), ⅛th inch (3.275 mm), and smaller diffraction gratings are considered in accordance with the present disclosure. Gratings can be cut from larger commercial gratings using a diamond saw or custom gratings can be purchased. Table 2 shows the grating grove densities required to give ~5 cm$^{-1}$ spectral resolution for gratings that range in size from 25.4 mm to 1.1 mm, using 785 nm, 532 nm and 244 nm excitation and that will give a spectral range of at least 4000 cm$^{-1}$, not considering Rayleigh diffraction effects from small optics. For the smaller grating sizes where Rayleigh diffraction must be considered the groove densities shown in Table 1 will be used as a starting point for optimization.

The small size of the optics in the interferometer can allow all critical components to be attached to a single substrate reducing effects of vibration on system stability. Alignment of optics on the collection side of the interferometer portion of the instrument is not critical. The alignment of detector imaging optics, while not as vibrationally sensitive as the interferometer optics, can be important to obtaining high contrast fringe images and high quality achromatic lenses can be mounted directly to the interferometer substrate. In previous designs, a relatively simple ray-tracing program, Beam 3©, has been utilized, to help optimize component layout. However, more sophisticated ray tracing and optics design software can be utilized to optimize component layout component selection and to determine component specifications for the miniature SHRSs. For this purpose, Zemax©, is one such suitable program. For miniature interferometer optics, optical tolerances and quality can be important and a sophisticated program like Zemax© can assist to optimize the design of the systems.

While spectral resolution is determined by the gratings in the SHS, the spectral range is determined by the number of pixels on the CCD or ICCD detector. Several commercial handheld Raman spectrometers are available that use small cooled CCDs with large numbers of small pixels and with noise sufficiently low to make Raman measurements. In accordance with the present disclosure, a conventional detector with 1024 or 2048 pixels can be utilized.

Several different types of lasers can be used in accordance with the present disclosure, including diode lasers for 785 nm, Nd:Yag and diode lasers for 532 nm and visible excitation, and intracavity-doubled argon-ion, tripled and quadrupled Nd:YAG, a hollow cathode laser, and LEDs for UV and deep UV.

TABLE 2

| Grating gr/mm | Grating width, mm | Spec. Res., $cm^{-1}$ 785 nm | Spec. Res., $cm^{-1}$ 532 nm | Spec. Res., $cm^{-1}$ 244 nm |
|---|---|---|---|---|
| 150 | 25.4 | — | — | 5.4 |
| 300 | 12.5 | — | 4.9 | 5.4 |
| 600 | 6.4 | — | 4.9 | 5.4 |
| 1200 | 3.2 | — | 4.9 | 5.4 |
| 1800 | 2.1 | — | 4.9 | 5.4 |
| 2400 | 1.6 | — | 4.9 | 5.4 |
| 300 | 4.2 | 5.0 | | |
| 600 | 2.1 | 5.0 | | |
| 1200 | 1.1 | 5.0 | | |

Note:
Spectral range for 785 nm, 532 nm, and 244 nm is 5134 $cm^{-1}$, 5062 $cm^{-1}$, and 5510 $cm^{-1}$, respectively at all grating sizes shown, using a 1024 pixel CCD and without wavelength doubling by vertical tilting of one diffraction grating. The resolving power is 2541, 3803 and 7616 for 785 nm, 532 nm, and 244 nm, respectively at all grating sizes shown. Diffraction effects from small optical components is not considered.

In accordance with the present disclosure, field-widening wedge prisms in the miniature SHRS can be utilized. Field widening prisms are easy to implement in the SHRS and can increase the acceptance angle from 1° without the prisms to as much as 10° using the prisms. This increased acceptance angle can result in an increased light throughout up to 100 times above the already high throughput of the SHS. Wedge prisms are placed between the beam splitter and gratings, so that, when the gratings are viewed from the output, they appear co-linear. The degree of field widening is a function of the prism refractive index and wedge angle and the angle of placement with respect to the incoming beam. The exact characteristics of the wedges can vary, however a relatively thin wedge with an angle of ~10-12° is typically used for up to 10° field widening, and wedges that are sufficiently flat ($\lambda/10$ or $\lambda/20$) for interferometry can be utilized. The addition of wedge prisms in the SHRS will not appreciably increase the overall size of the spectrometer.

The light throughput is related to system sensitivity for any optical system. A measure of light throughput is optical etendue, which is area times collection solid angle, see Eqns. 2 and 3, and the sensitivity of a given spectrometer is determined by the limiting etendue component in the system. The light throughput for the basic SHRS spectrometers described above will be a hundred times higher than current dispersive Raman spectrometers, and even higher when field widening prisms are used. This is illustrated by comparison to one of the fastest Raman spectrometers commercially available, an F/1.8 volume holographic Raman spectrometer (Kaiser Holospec F/1.8). This system gives ~15 $cm^{-1}$ spectral resolution using a 100-micron slit. Using Eqns. 2 and 3 to calculate the spectrometer etendue, gives $1.9 \times 10^{-5}$ $cm^2 \cdot sr$. The etendue of the SHRS will depend on the grating size and whether or not field-widening prisms are used. One example can be 0.12 $cm^2 * sr$ using 12.7 mm gratings and 10° field widening prisms (~6300 times higher than the F/1.8 spectrometer), while another example is $7.5 \times 10^{-5}$ $cm^2 * sr$ using 3.2-mm gratings with no field widening prisms. Even in the latter example, the 3.2-mm grating SHRS provides ~4 times higher throughput than the currently available Raman system and in a package that is thousands of times smaller than the commercial system. For many applications, field widening prisms can be used for the smaller system making the light throughput for even the 3.2-mm SHRS about 400 times higher than the commercial F/1.8 Raman spectrometer.

$$E = A\Omega \qquad \text{Eqn. 2}$$

$$\Omega = \pi/4 * (F/\#)^2 \qquad \text{Eqn. 3}$$

The large acceptance angle of the SHRS can make fiber coupling much more efficient than existing Raman spectrometers. Fiber-optic coupling is routinely used to connect a Raman spectrometer to a sampling area or to a sampling device such as a microscope. However fiber-optic coupling is not a trivial exercise and is inherently lossy because of the high numerical aperture (e.g., NA) of commercial fiber optics. A typical optical fiber has a numerical aperture of about 0.242, (F/2) and an acceptance angle of about 14°. It is because of this large NA that several Raman spectrometer manufacturers have developed systems with F/2 or faster collection optics. However, collection angle alone is not enough to ensure efficient coupling of light from an optical fiber to a spectrometer. The optical etendue is a measure of how much light can be coupled through the optical system and the limiting etendue determines overall system sensitivity. The etendue for a 1-mm diameter, F/2 optical fiber would be $~1.5 \times 10^{-3}$ $cm^2 \cdot sr$, where the collection solid angle is calculated using Eqn. 3. But the etendue of a typical F/2 dispersive Raman spectrometer using a 100-micron slit (e.g., ~15 $cm^{-1}$ resolution) is only about $1.54 \times 10^{-5}$ $cm^2 \cdot sr$, or 100 times smaller than the fiber throughput. Most of the light collected and transmitted by the fiber would be lost at the slit of the spectrometer. No matter how the light is coupled between the optical fiber and the spectrometer this will be true because the etendue is invariant in any optical system. A smaller optical fiber can be used to match the dispersive spectrometer slit, but the effect would be the same, only $1.54 \times 10^{-5}$ $cm^2 * sr$ total light throughput. In addition, using such small optical fibers requires complex optics and filtering as can be seen in any high-quality commercial fiber-optic Raman probe.

Calculating the coupling efficiency of the same 1-mm, F/2 optical fiber to the SHRS gives a completely different result. An SHRS with 1.42-mm gratings and 10° field widening prisms has an etendue of almost exactly $1.5 \times 10^{-3}$ $cm^2 * sr$, the same as the 1-mm diameter, F/2 optical fiber, so no light would be lost coupling the two—note they are of comparable size. Even using a 3.2-mm grating SHRS without field widening prisms, would provide ~5 times more light coupled between the optical fiber and the SHRS, in a package orders of magnitude smaller than a dispersive Raman spectrometer of similar resolution and range. As such, greatly improved fiber-optic coupling efficiency is an advantage of the miniature SHRS of the present disclosure.

The systems of the present disclosure can be used to measure Raman spectra of explosive gas mixtures in a capillary waveguide to demonstrate the advantages of the high light throughout, wide-angle acceptance and wide-area measurement capability and the high spectral resolution and range of the miniature SHRS spectrometers described herein. Measurement of gases can be used to demonstrate the miniature SHRS devices because gases are among the most difficult to measure Raman samples because of the low molecular density, high spectral resolution requirements, and there are many important applications related to gas measurements.

$$x_e = \left( \frac{1 - e^{-(\alpha_L \alpha_R x_p)}}{(\alpha_L \alpha_R)} \right).$$

The measurement of gases using Raman spectroscopy is well established and many important gases, including hydrogen, nitrogen, and oxygen, which are homo-nuclear and thus cannot be measured by infrared spectroscopy, are Raman active. These gases are also difficult to measure directly by other means, and in applications where sampling and physical contact with the sample isn't allowed (e.g., remote atmospheric measurements, combustible gas analysis, aerospace and planetary applications, wind tunnel measurements, medical applications, etc.), Raman spectroscopy can be the preferred method. A simple multipass capillary Raman cell (MCC) for Raman gas measurements has been recently described that is amenable to remote and in situ operation and that requires very little optical alignment. The cell includes a small diameter, 1 to 2-mm capillary tube that is coated on the inside with silver, a highly reflective metal. The cell is coupled to a spectrometer by simply inserting the tip of a fiber-optic probe into one end of the cell. The Raman signal is enhanced by up to 30-fold because of an effective path length increase given by Eqn. 4, where $\alpha_L$ and $\alpha_R$ are the loss coefficients at the laser and Raman wavelengths, respectively, and $x_p$ is the physical length of the capillary. However, the actual Raman signal that is collected for a given gas and MCC geometry is more complicated. As previously described, the maximum Raman signal that could be collected from the MCC was limited by the largest diameter fiber-optic probe that could be efficiently coupled to the F/1.8 Raman spectrometer (Kaiser Holospec f/1.8), and it was shown that the Raman signal was larger for larger diameter MCCs.

Figure 7:
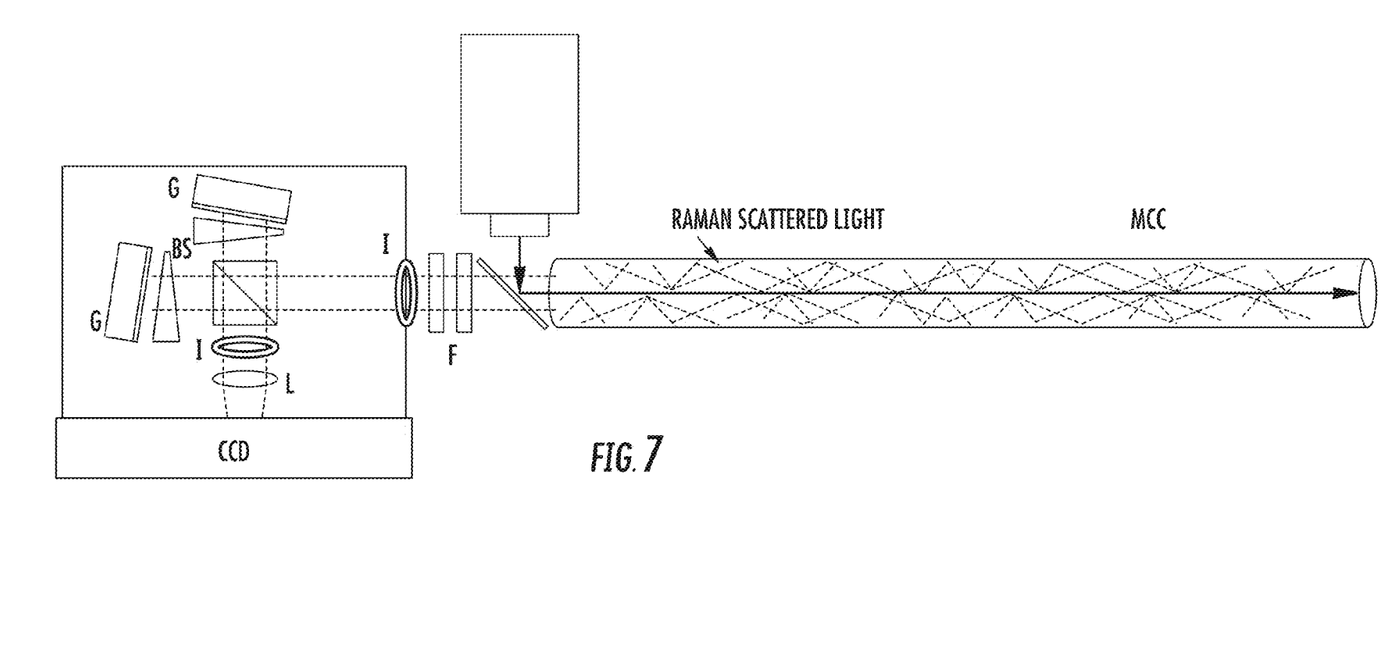
FIG. 7 depicts SHRS coupled to a multipass capillary Raman cell for gas measurements in accordance with certain aspects of the present disclosure.

MCC gas measurements are an ideal application to demonstrate the capabilities of a miniature SHRS—the spectrometer can be as small as the capillary waveguide. FIG. 7 illustrates how an SHRS can be coupled to a multipass capillary Raman cell for gas measurements. No optics will be needed between the SHRS and the small-diameter (2-5 mm) MCC. Field widening prisms in the SHRS can be used for a collection angle of ~10°. Though this is less than the 14° collection angle for a typical optical fiber, as described above the greater throughput of the SHRS can provide a signal that is up to 100 times larger than the previously described fiber-coupled spectrometer. Different sizes of SHRSs and different diameter MCCs can be utilized to determine the sensitivity for measuring explosives gas mixtures. Since the previously described MCC results showed gas detection limits that were better than conventional systems for Raman, using the SHRS for a number of different gases such as $H_2$, $O_2$, butane, methane, and others can exceed current reported detection limits. The MCC can also be utilized to review rotational Raman with the SHRS of these gases. In particular, a system with sufficient spectral resolution to resolve rotational structure (e.g., <5 cm$^{-1}$) can be utilized. Fiber-optic coupling of the SHRS and MCC is straightforward as described above. The SHRS can allow much larger fibers and much larger MCCs than could be used previously. The use of image reduction fibers can match the SHRS output to the CCD. The use of fiber-optic image guides can couple the interferometer fringe image to a remotely located CCD. This capability can assist to produce miniature SHRSs as described herein that can be incorporated into chemical reaction streams, directly on a confocal microscope to add a Raman chemical mapping or imaging capability, into microchannel and microfluidic devices for on-line chemical sensing and imaging and for chemical sensing in additive manufacturing. These things could be done at a fraction of the complexity of current systems and without the need to wait for further miniaturization of CCD detectors.

The SHRS as described above can be modified very simply for spatial imaging by focusing the image of a Raman source onto the grating plane. An imaging SHS can be accomplished by placing imaging lenses one focal length from the grating, between the beam splitter and each diffraction grating. 1D imaging is straightforward with this configuration and 2D imaging can be accomplished by scanning the source image across the grating plane.

An SHS Raman spectrometer is an excellent candidate for microRaman and chemical mapping of concentration gradients and diffusion and because there are no moving parts all wavelengths are measured simultaneously making it useful for fast, time resolved measurements. A tremendous advantage of the SHRS design is the ability to measure very wide areas. As an example, the field of view of the SHRS is given by $\tan(\theta)$=FOV/F, where $\theta$ is the acceptance angle and F is the focal length of the lens used to collect Raman photons from a source and illuminate the entrance aperture of the SHRS. If a 5-mm diameter, 20-mm focal length lens (e.g., F/4) is used to collect light from a capillary mixing chamber, the FOV would be 3.5 mm using a 5-mm grating, 10° field widened UV SHRS and the spatial resolution in the imaging dimension would be ~7 microns using a 512 element CCD with 5 cm$^{-1}$ spectral resolution. The same measurement using a typical high throughput UV spectrometer (F/6.5, Acton Model i2500) with 20-micron slits (~15 cm$^{-1}$ resolution), and the same F/4 collection lens would have a FOV of 0.012-mm. The wide FOV of the SHRS can be used for high spatial resolution wide area imaging. But there is another advantage of a wide FOV. Using the same laser power, a large FOV minimizes laser-induced sample damage and heating with no reduction in Raman signal.

Figure 8:
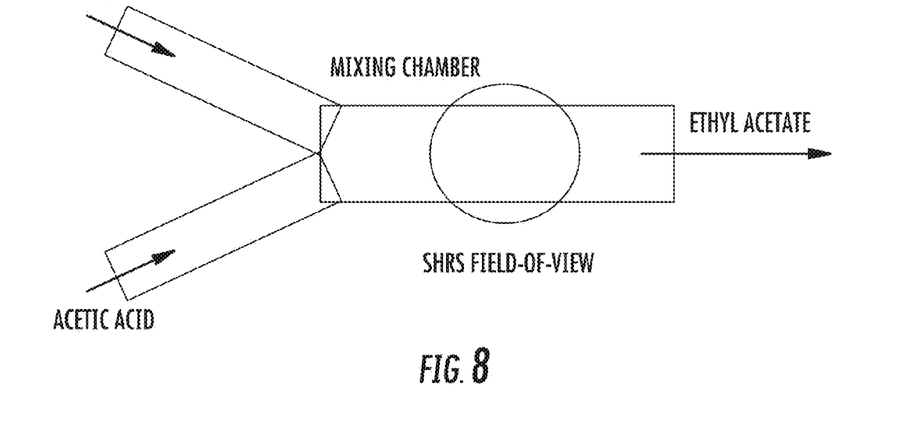
FIG. 8 depicts a capillary syringe pump used to deliver reagents into a fused heated silica capillary reaction cell in accordance with certain aspects of the present disclosure.

The reaction of ethanol and acetic acid to produce ethyl acetate can be used to demonstrate Raman for chemical reaction monitoring. The reaction is very clean, and Raman bands of both reactants and products are well resolved. A capillary syringe pump can be used to deliver reagents into a fused heated silica capillary reaction cell (as illustrated in FIG. 8). The SHRS in an imaging configuration can be set to view the reaction chamber so that the field of view is larger than the mixing cell, with spatial resolution across the cell. Rate of reaction versus sample temperature can be measured under different flow conditions of reactants and at different positions along the capillary. In laminar flow where rate of reactant mixing is diffusion controlled, time-resolved 1D Raman images allows diffusion constants to be determined.

Figure 9:
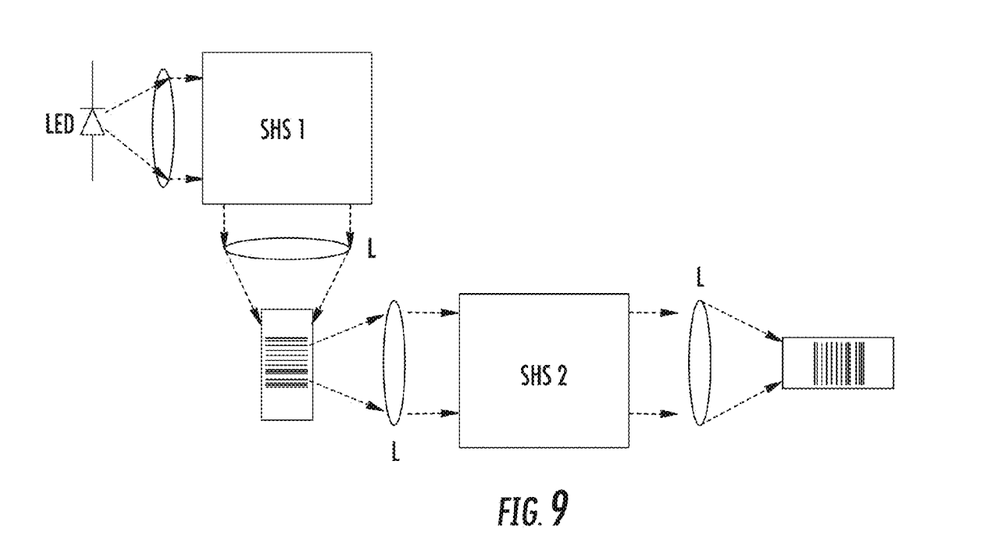
FIG. 9 depicts LED light collimated and sent into an SHS rotated to give horizontal fringes which are imaged onto the sample, where L=lens, the resulting sample scattered light is collected and collimated and sent into a second SHS which is orthogoinal to the first to give vertical fringes; the vertical fringes are imaged onto a 2D CCD detector; a 2D Fourier transform can be capable of deconvoluting the LED spectral intensities from the sample Raman bands, all in accordance with certain aspects of the present disclosure.

High power UV LEDs are available at UV wavelengths as short as 250 nm. However, they are not suitable for Raman measurements using dispersive Raman spectrometers because of the broad-band LED emission, about 3 nm, and because they are diffuse sources that cannot be focused to a small spot. The output light of a high power LED could be dispersed, and the dispersed light focused onto a sample so that different wavelengths illuminate different parts of the sample in a vertical strip. Raman scattered light from the illuminated region could be collected through the slit of a monochromator and spatially resolved by the CCD so that different excitation wavelengths produce Raman spectra at different vertical positions on the CCD. The spatially resolved spectra could then be corrected for excitation wavelength and co-added to produce a single high signal-to-noise Raman spectrum. Generally, such a method may not work well for a slit-based detection system because of the large spot produced on the sample. As described above however, the wide field of view of the SHRS in a 1D imaging configuration can eliminate the need to tightly focus the LED. A solution to this problem is to use the LED to illuminate the input aperture of a SHS, rotated 90° to the normal configuration, to produce a series of horizontal fringes running vertically on the sample, as shown in FIG. 9. Scattered light from the sample would be focused on a 1D imaging SHRS, a 1D Fourier transform of the resulting interferogram produce a series of Raman spectra with the encoded interferogram of the LED. A 2D Fourier transform of the interferogram should deconvolute the Raman spectra and excitation wavelengths, producing a 2D Raman map of Raman spectra. versus excitation wavelength. Such a technique can use the full power of the LED and can greatly expand the range of Raman applications and potentially reduce the cost of Raman instruments.

Figure 10:
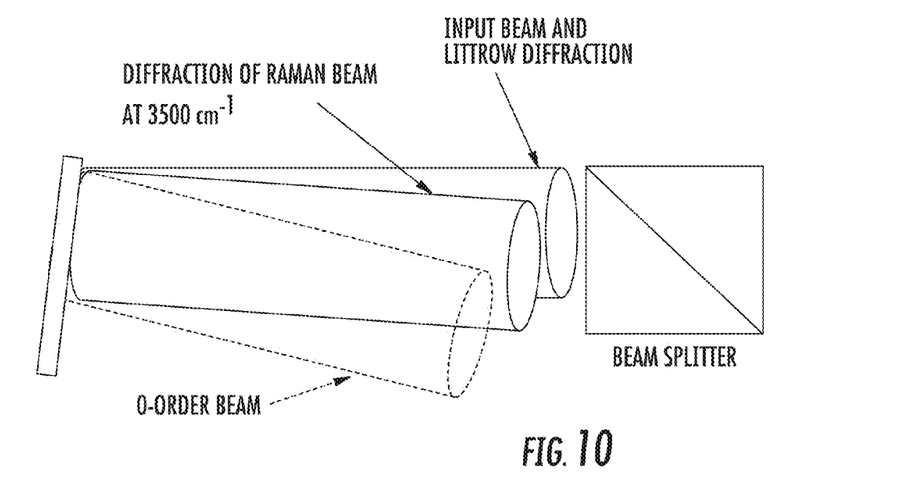
FIG. 10 depicts the relationship between the incoming beam, the Littrow diffracted beam, the diffracted beam for a 3500 cm$^{-1}$ Raman band and o-order reflection (only one diffraction grating is shown, for clarity) in accordance with certain aspects of the present disclosure.
Figure 11:
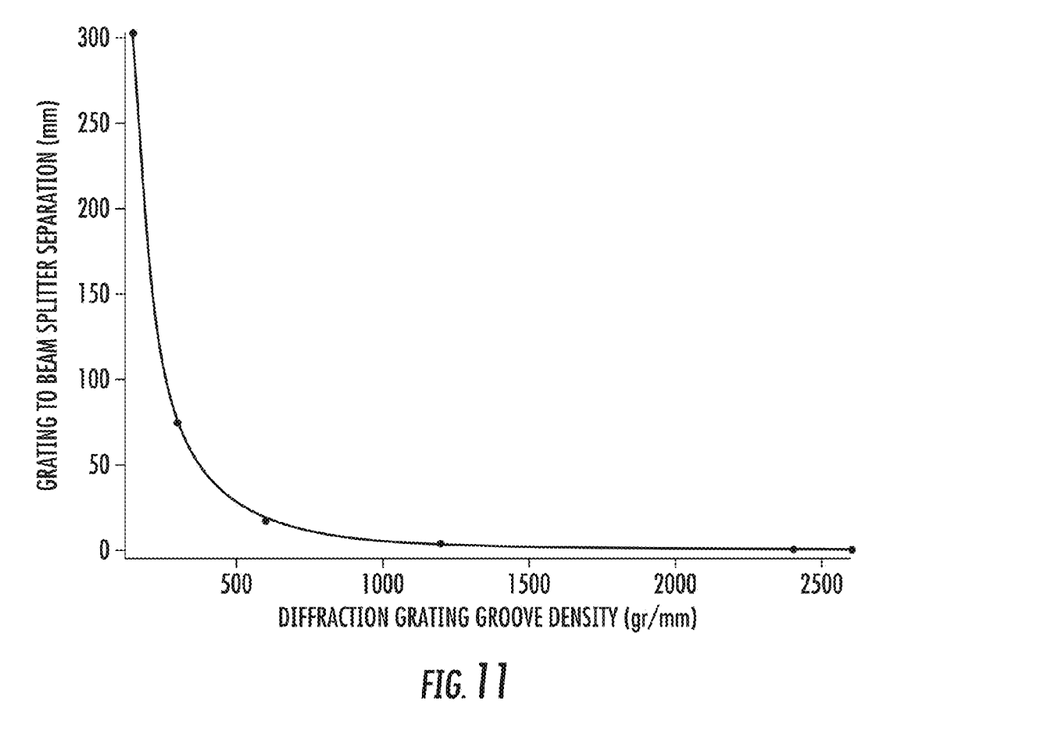
FIG. 11 depicts a plot of the separation distance between the diffraction grating and the beam splitter versus the grating grove density in accordance with certain aspects of the present disclosure.

The size of the SHRS depends on the size of the grating and beam splitter but also on the separation between them. The minimum separation between grating and beam splitter is the distance that prevents 0-order and 2nd-order diffraction from the grating from entering the beam splitter, as shown in FIG. 10. As described previously, using 25.4 mm, 150 gr/mm gratings the required separation was about 300 mm. It can be shown that the grating to beam splitter minimum separation decreases rapidly, roughly as the square of the grating size, because as the grating size is decreased, the groove density also increases to maintain a constant 5 cm$^{-1}$ resolution, resulting in a larger Littrow angle and greater separation of the Raman beam from 0-order and 2nd-order beams. Table 3 shows calculations of the minimum grating to beam splitter separation, y, and the Littrow angle for different size gratings, where the groove density is increased to maintain constant resolving power. The results plotted in FIG. 11 show how the SHRS footprint decreases with grating size. Table 3 also shows the special case of a 45° Littrow angle where there is no 0-order or 2nd-order diffraction and zero required separation between the gratings and the beam splitter.

TABLE 3

Distance between grating and beam splitter and Littrow angle of 5-cm$^{-1}$ resolution interferometer (footprint mm) for different groove density and grating sizes for the condition of no 0- or 2nd order grating overlap on the CCD, using 532 nm excitation and for a 400 cm$^{-1}$ Raman shift.

| Gr/mm | Littrow angle | Size (mm) | y |
|---|---|---|---|
| 150 | 2.4° | 25.4 | 303 |
| 300 | 4.84° | 12.7 | 75 |
| 600 | 9.69° | 6.35 | 18 |
| 1200 | 19.7° | 3.175 | 3.9 |
| 2400 | 42.5° | 1.588 | 0.14 |
| 2602* | 45° | 1.464 | 0* |

*indicates the special case of 45° diffraction where no 0- or 2nd-order leaves the diffraction grating and the gratings are physically attached or engraved directly on the beam splitter.

In accordance with the present disclosure, potential applications of the systems and methods described herein include the ability to integrate micro SHS device(s) into a manufacturing process. For instance, such devices could be used in an additive manufacturing instrument, or in a microfluidic device sensor, or a gas stream or other on-line chemical monitoring stream. Or one or more devices can be placed on the end of a robot arm on a planetary spacecraft such as on a lander or to fly through a comet. Another application is to use a coherent image reduction fiber bundle to match the size of the micro-SHS to a larger CCD detector.

While the present subject matter has been described in detail with respect to specific exemplary embodiments and methods thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A device comprising:
   an excitation source;
   a first spatial heterodyne spectrometer configured to receive wavelengths from the excitation source and filter the wavelengths to produce fringes on a sample;
   a second spatial heterodyne spectrometer configured to receive Raman wavelengths from the sample.

2. The device of claim 1, wherein the excitation source is a light emitting diode.

3. The device of claim 1, further comprising one or more band pass filters, the one or more band pass filters being configured to remove light outside of the Raman wavelengths.

4. The device of claim 1, further comprising one or more blocking filters.

5. The device of claim 1, further comprising a charge coupled device or intensified charge coupled device configured to collect Raman wavelengths.

6. The device of claim 1, wherein the first spatial heterodyne spectrometer further comprises a diffraction grating or dispersive prism, the grating or prism configured to adjust the wavelengths.

7. The device of claim 6, wherein the grating angle can be adjusted.

8. The device of claim 7, wherein the first spatial heterodyne spectrometer comprises one or more simple wedge prisms to further increase the acceptance angle.

9. A method for spectroscopy comprising:
   producing fringes on a sample with a first spatial heterodyne spectrometer, the first spatial heterodyne spectrometer receiving wavelengths from an excitation source and filter the wavelengths to produce the fringes on the sample; and
   utilizing a second spatial heterodyne spectrometer to receive Raman wavelengths from the sample.

10. The method of claim 9, further comprising one or more band pass filters, the one or more band pass filters removing light outside the Raman wavelengths.

11. The method of claim 9, further comprising one or more detectors, the one or more detectors detecting ambient light, vibrational instabilities, or combinations thereof.

12. The method of claim 9, wherein the spatial heterodyne spectrometer further comprises a diffraction grating or prism, the grating or prism being moved to adjust the wavelengths.

13. The method of claim 9, further comprising utilizing the second spatial heterodyne spectrometer to perform time-resolved Raman spectroscopy.

14. The method of claim 9, wherein the excitation source is a light emitting diode.

15. The method of claim 9, wherein Stokes and anti-Stokes Raman wavelengths are measured simultaneously.

16. The method of claim 9, further comprising determining the sample temperature.

17. The method of claim 9, wherein the sample comprises biomarker, mineral, rock, ice, light sensitive material, or combinations thereof.

18. The method of claim 9, wherein the sample comprises a high explosive.

19. The method of claim 9, wherein the second spatial heterodyne spectrometer is configured as a microRaman device for point measurements or imaging to produce chemical maps.

20. The method of claim 9, wherein the second spatial heterodyne spectrometer is configured as an in-situ chemical sensor to obtain chemical information that is capable of being utilized for chemical reaction control or additive manufacturing.

21. The method of claim 9, wherein the second spatial heterodyne spectrometer is utilized to perform analysis on multiple spectroscopies.

* * * * *